(12) United States Patent
Himmler et al.

(10) Patent No.: US 9,365,586 B2
(45) Date of Patent: Jun. 14, 2016

(54) METHOD FOR PRODUCING DITHIINE TETRACARBOXIMIDES

(71) Applicants: BAYER CROPSCIENCE AG, Monheim (DE); BAYER INTELLECTUAL PROPERTY GMBH, Monheim (DE)

(72) Inventors: Thomas Himmler, Odenthal (DE); Thomas Geller, Odenthal (DE); Lars Rodefeld, Leverkusen (DE); Mark James Ford, Schmitten (DE); Guenter Hoemberger, Eppstein (DE); Dieter Heinz, Bergisch Gladbach (DE)

(73) Assignees: Bayer Cropscience AG, Monheim (DE); Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/385,648

(22) PCT Filed: Mar. 18, 2013

(86) PCT No.: PCT/EP2013/055565
§ 371 (c)(1),
(2) Date: Sep. 16, 2014

(87) PCT Pub. No.: WO2013/139736
PCT Pub. Date: Sep. 26, 2013

(65) Prior Publication Data
US 2015/0045561 A1    Feb. 12, 2015

(30) Foreign Application Priority Data

Mar. 23, 2012 (EP) .................................... 12161009

(51) Int. Cl.
*C07D 495/14* (2006.01)
(52) U.S. Cl.
CPC .................................. *C07D 495/14* (2013.01)
(58) Field of Classification Search
CPC .................................................. C07D 495/14
See application file for complete search history.

(56) References Cited

U.S. PATENT DOCUMENTS

| | | | |
|---|---|---|---|
| 3,364,229 A | 1/1968 | Draber et al. | |
| 8,450,360 B2* | 5/2013 | Himmler | C07D 495/14 514/411 |
| 8,524,916 B2* | 9/2013 | Himmler | C07D 495/14 548/431 |
| 8,609,868 B2* | 12/2013 | Lui | C07D 495/14 548/431 |
| 8,658,565 B2* | 2/2014 | Seitz | A01N 43/90 504/100 |
| 8,669,372 B2* | 3/2014 | Himmler | C07D 495/04 548/431 |
| 8,729,275 B2* | 5/2014 | Himmler | C07D 207/456 548/431 |
| 8,865,759 B2* | 10/2014 | Seitz | C07D 495/14 514/411 |
| 8,916,500 B2* | 12/2014 | Seitz | A01N 43/32 504/100 |
| 9,006,139 B2* | 4/2015 | Seitz | A01N 43/90 504/100 |
| 9,012,362 B2* | 4/2015 | Seitz | A01N 43/90 424/605 |
| 9,018,132 B2* | 4/2015 | Seitz | A01N 43/90 504/100 |
| 9,095,140 B2* | 8/2015 | Seitz | A01N 43/90 |
| 2010/0120884 A1* | 5/2010 | Seitz | C07D 495/14 514/411 |
| 2011/0269973 A1 | 11/2011 | Himmler et al. | |
| 2011/0280958 A1* | 11/2011 | Seitz | A01N 43/90 424/632 |
| 2011/0319462 A1* | 12/2011 | Seitz | C07D 495/14 514/411 |
| 2014/0256956 A1* | 9/2014 | Himmler | C07D 495/04 548/431 |

FOREIGN PATENT DOCUMENTS

| | | |
|---|---|---|
| CN | 1884282 A | 12/2006 |
| JP | 10251265 A | 9/1998 |
| PL | 143804 B2 | 10/1985 |
| WO | 2011128263 A1 | 10/2011 |

OTHER PUBLICATIONS

International Search Report from corresponding PCT/EP2013/055565, mailed May 23, 2013.
Draber, "Synthese von 1.4-Dithiienen aus Derivaten des Maleinimids", Chem. Ber. 100, pp. 1559-1570 (1967).
Zentz et al., "Syntheses, in vitro antibacterial and antifungal activities of a series of N-alkyl, 1,4-dithiines", Il Farmaco, 60:11-12 (2005) pp. 944-947 , XP027697616.
Katritzky et al., "Some Novel Quinone-Type Dyes Containing Naphthoquinone and Related Fused Ring Sysems", J. Heterocyclic Chem., 25, 901, May-Jun. 1988, pp. 901-906.
Gulten, "The Synthesis and Characterization of Solvatochromic Maleimide-Fused N-Ally- and N-Alkyl-Substituted 1,4-Dithiines and Diels-Alder Reactions and Anthracene", J. Heterocyclic Chem., vol. 47, (2010), pp. 188-193.
Valla, et al. "Atypical Oxidation Reaction by Thionyl Chloride: Easy Two-Step Synthesis of N-Alkyl-1,4-dithiines", Synthetic Communicationsw, 36:23, pp. 3591-3597, 2006, XP002599895.

* cited by examiner

*Primary Examiner* — Nyeemah A Grazier
(74) *Attorney, Agent, or Firm* — McBee Moore Woodward Vanik IP, PLLC

(57) ABSTRACT

The present invention relates to a process for preparing dithiinetetracarboximides by reaction of succinic monoamides with thionyl chloride, with continuous performance of at least one of the process steps.

14 Claims, 1 Drawing Sheet

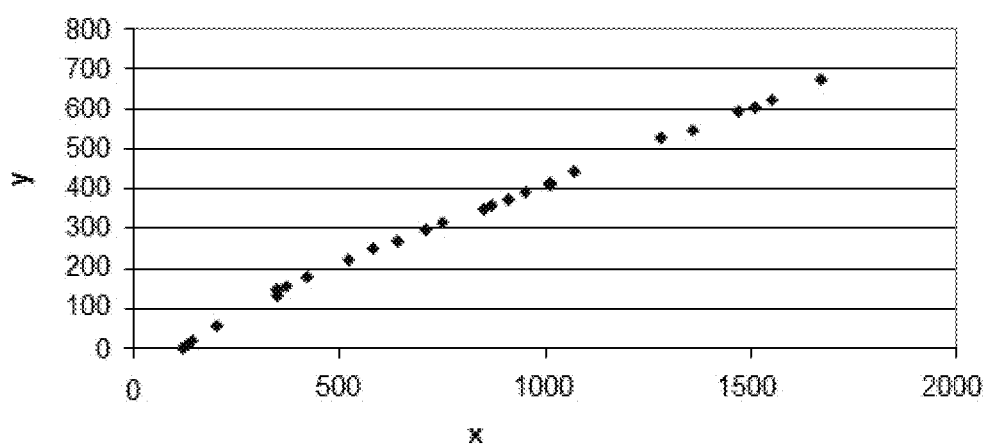

METHOD FOR PRODUCING DITHIINE TETRACARBOXIMIDES

CROSS REFERENCE TO RELATED APPLICATIONS

This application is a §371 National Stage Application of PCT/EP2013/055565, filed Mar. 18, 2013, which claims priority to EP 12161009.1, filed Mar. 23, 2012.

BACKGROUND

1. Field of the Invention

The present invention relates to a process for preparing dithiinetetracarboximides by reaction of succinic monoamides with thionyl chloride, with continuous performance of at least one of the process steps.

2. Description Of Related Art

Dithiinetetracarboximides as such are already known. It is likewise known that these dithiinetetracarboximides can be used as anthelmintics to counteract internal parasites in animals, especially nematodes, and have insecticidal action (cf. U.S. Pat. No. 3,364,229). It is also known that particular dithiinetetracarboximides have antibacterial action and have a certain effect against organisms which cause human mycoses (cf. Il Farmaco 2005, 60, 944-947). It is additionally known that dithiinetetracarboximides can be used as pigments in electrophotographic photoreceptors or as dyes in coatings and polymers (cf. JP-A 10-251265, PL-B 143804).

Dithiinetetracarboximides of the formula (I)

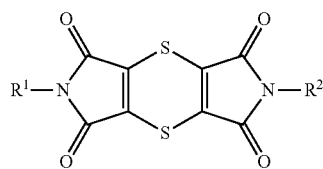

in which

R$^1$ and R$^2$ are the same or different and are each hydrogen, optionally mono- or poly-halogen-, —OR$^3$—, —COR$^4$—substituted C$_1$-C$_8$-alkyl, optionally mono- or poly-halogen-, —C$_1$-C$_4$-alkyl- or —C$_1$-C$_4$-haloalkyl-substituted C$_3$-C$_7$-cycloalkyl, in each case optionally mono- or poly-halogen-, —C$_1$-C$_4$-alkyl-, —C$_1$-C$_4$-haloalkyl-, —COR$^4$— or -sulphonylamino-substituted aryl or aryl-(C$_1$-C$_4$-alkyl), R$^3$ is hydrogen, C$_1$-C$_4$-alkyl, C$_1$-C$_4$-alkylcarbonyl or optionally mono- or poly-halogen-, —C$_1$-C$_4$-alkyl- or —C$_1$-C$_4$-haloalkyl-substituted aryl, R$^4$ is hydroxyl, C$_1$-C$_4$-alkyl or C$_1$-C$_4$-alkoxy, can be prepared in various known ways.

For example, in one process (cf. U.S. Pat. No. 3,364,229; Chem. Ber. 1967, 100, 1559-1570), in a first stage, dichloromaleic anhydride of the formula (II) is reacted with an amine of the formula (III), optionally in the presence of a diluent. Subsequently, the dichlormaleimides of the formula (IV) thus obtained are reacted with a sulphur compound (e.g. hydrogen sulphide or thiourea). The preparation of the dithiinetetracarboximides of the formula (I) by this process can be illustrated by the following scheme:

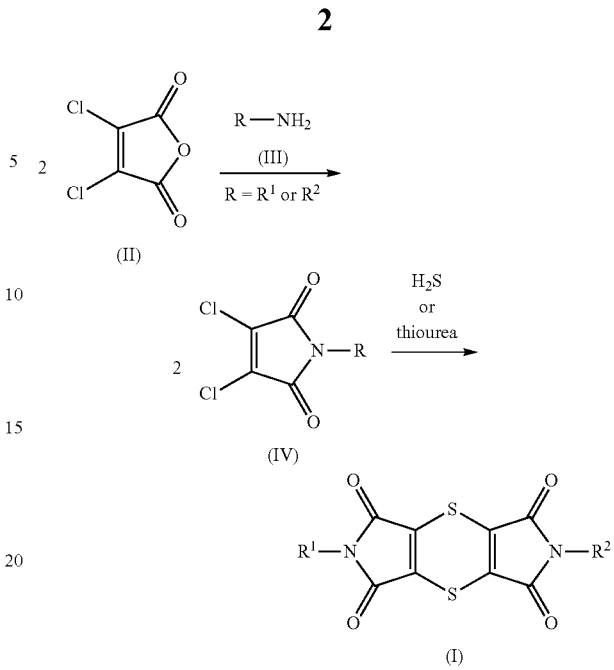

This process has the disadvantage that, for example, the handling of hydrogen sulphide gas, which is highly toxic, is technically very difficult and inconvenient. In the case of use of thiourea, apart from the target product, unwanted by-products are obtained, these being removable only with very great difficulty and worsening the yields achievable (cf. J. Heterocycl. Chem. 1988, 25, 901-906).

In a further process which has become known (cf. Synthetic Communications 2006, 36, 3591-3597), in a first stage, succinic anhydride of the formula (V) is reacted with an amine of the formula (III), optionally in the presence of a diluent. Subsequently, the succinic monoamides of the formula (VI) thus obtained are reacted with a large excess of thionyl chloride in the presence of dioxane as a diluent at room temperature for 6 hours, the dithiinetetracarboximides of the formula (I) finally being obtained in a sequence of numerous reaction steps. The dithiinetetracarboximides are either isolated directly from the reaction mixture or by filtration after addition of water. According to the reaction conditions (diluent) and nature of the R radicals, under some circumstances, the dithiinediisoimides of the formula (VII) can be isolated before they are converted to the dithiinetetracarboximides of the formula (I). This method for preparing the dithiinetetracarboximides of the formula (I) can be illustrated by the following scheme:

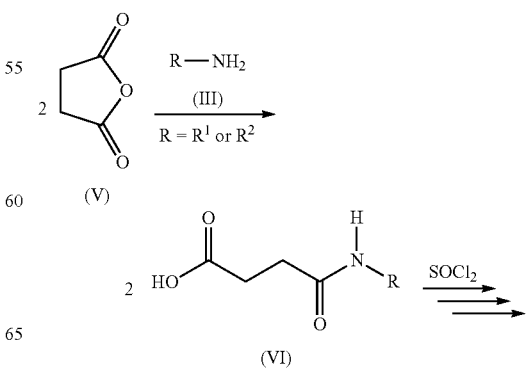

-continued

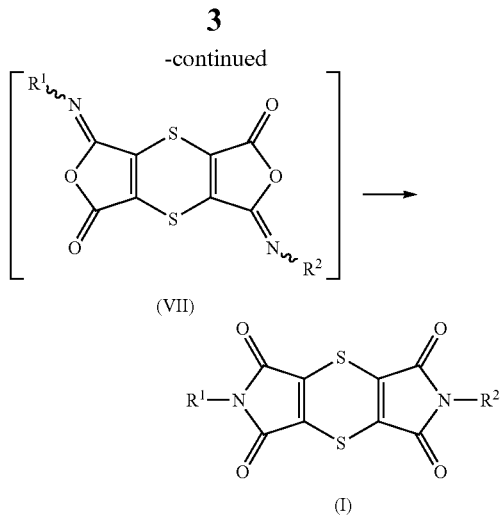

(VII)

(I)

Disadvantages of this process are the long reaction time and the result that either the yields obtained generally do not exceed about 30-40% of theory, or else the purities of the isolated products are inadequate. Another disadvantage in the case of aqueous workup of the reaction mixture is that large amounts of thionyl chloride are destroyed; the gases which arise ($SO_2$ and HCl) have to be disposed of. Likewise disadvantageous is the fact that, as experience has shown, the product is not obtained in one fraction. Instead, it is frequently the case that, after a first product isolation by filtration further product precipitates out of the filtrate after standing for a prolonged period (for example overnight), and this has to be isolated by filtration again. Sometimes, this operation has to be performed once again. This way of working is very inconvenient and time-consuming.

It is additionally known that dithiinetetracarboximides are obtained by dissolving N-substituted succinamides in dry 1,4-dioxane and then admixed with thionyl chloride. Subsequently, the reaction mixture is heated and the solution is concentrated in vacuo and separated and purified by means of column chromatography (cf. J. Heterocycl. Chem. 2010, 47, 188-193).

It is additionally known that dithiinetetracarboximides are obtained by admixing N-substituted succinamides with thionyl chloride, optionally in the presence of an inert diluent. Subsequently, the excess thionyl chloride is distilled off, and the remaining reaction mixture is heated in the presence of water and optionally in the presence of an inert diluent (cf. WO 2011/128263).

The prior art processes, however, have the following disadvantages:
a) the low space-time yield,
b) the large excess of thionyl chloride based on the succinic monoamides, which requires a high level of technical complexity in the workup of the reaction output and recovery of the unconverted thionyl chloride and hence high capital and energy costs,
c) the offgas flow released in the reaction does not run homogeneously and hence makes it difficult to implement a technically simple and economic preparation process possibly including the simultaneous reprocessing of the offgas stream for the purpose of reutilization.

SUMMARY

It was thus an object of the present invention to provide a technically simple and economic preparation process for dithiinetetracarboximides of the formula (I) in high yields and space-time yields and high quality.

It has been found that, surprisingly, the compounds of the formula (I)

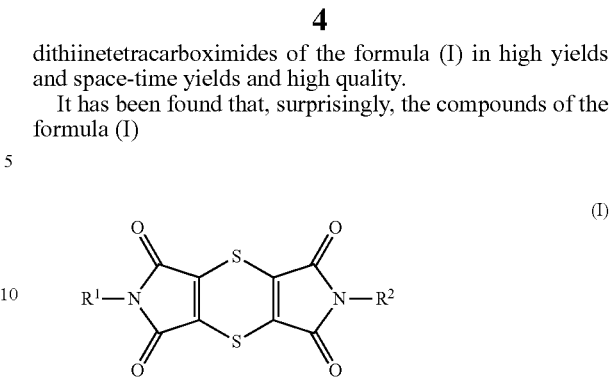

in which
$R^1$ and $R^2$ are the same or different and are each hydrogen, optionally mono- or poly-halogen-, —$OR^3$—, —$COR^4$—substituted $C_1$-$C_8$-alkyl, optionally mono- or poly-halogen-, —$C_1$-$C_4$-alkyl- or -$C_1$-$C_4$-haloalkyl-substituted $C_3$-$C_7$-cycloalkyl, in each case optionally mono- or poly-halogen-, —$C_1$-$C_4$-alkyl-, —$C_1$-$C_4$-haloalkyl-, —$COR^4$— or -sulphonylamino-substituted aryl or aryl-($C_1$-$C_4$-alkyl),
$R^3$ is hydrogen, $C_1$-$C_4$-alkyl, $C_1$-$C_4$-alkylcarbonyl or optionally mono- or poly-halogen-, —$C_1$-$C_4$-alkyl- or —$C_1$-$C_4$-haloalkyl-substituted aryl,
$R^4$ is hydroxyl, $C_1$-$C_4$-alkyl or $C_1$-$C_4$-alkoxy,
are obtained both in high yield and in high space-time yield when at least one of the process steps is conducted continuously.

DETAILED DESCRIPTION OF A PREFERRED EMBODIMENT

Hereinabove and hereinbelow, the term "continuously" means a procedure in which reaction media are present in a flow system, and are passed through particular functional zones, especially mixing zones, reaction zones and dwell zones. The reactants are supplied within defined units of time and the products are removed within defined units of time.

Hereinabove and hereinbelow, the term "reactant" means a chemical compound which is processed further in a downstream reaction step. This term includes both chemical compounds which are being newly introduced into the overall process and those which have been obtained in an upstream process and are being processed further.

The present invention provides a process for preparing dithiinetetracarboximides of the general formula (I)

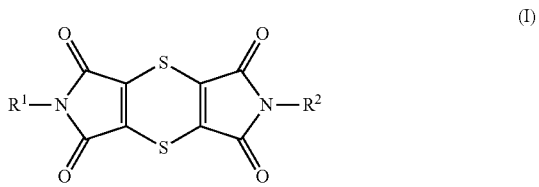

in which
$R^1$ and $R^2$ are the same or different and are each hydrogen, optionally mono- or poly-halogen-, —$OR^3$—, —$COR^4$-substituted $C_1$-$C_8$-alkyl, optionally mono- or poly-halogen-, —$C_1$-$C_4$-alkyl- or —$C_1$-$C_4$-haloalkyl-substituted $C_3$-$C_7$-cycloalkyl, in each case optionally mono- or poly-halogen-, —$C_1$-$C_4$-alkyl-, —$C_1$-$C_4$-haloalkyl-, —$COR^4$— or -sulphonylamino-substituted aryl or aryl-($C_1$-$C_4$-alkyl), $R^3$ is hydrogen, $C_1$-$C_4$-alkyl, $C_1$-$C_4$-alkylcarbonyl or optionally mono- or poly-halogen-, —$C_1$-$C_4$-alkyl- or —$C_1$-$C_4$-haloalkyl-substituted aryl, $R^4$ is hydroxyl, $C_1$-$C_4$-alkyl or $C_1$-$C_4$-alkoxy, characterized in that, in a first stage (1), succinic monoamides of the formula (VI)

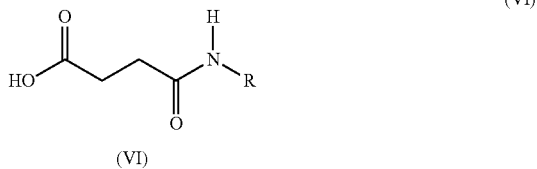

(VI)

in which R is $R^1$ or $R^2$, are reacted with thionyl chloride to give a reaction mixture, the reaction mixture formed is heated in a second stage (2), and then the reaction mixture is converted to the dithiinetetracarboximides in the third step (3), with continuous performance of at least one of the three steps.

Preferably, in the process according to the invention, the sum total of thionyl chloride (z) is between 2.5 and 20 mol per mole of succinic monoamide of the formula (VI), where z is defined by the relationship $$z = x + y$$

and z is the total amount of thionyl chloride (mol of thionyl chloride per mole of succinamide of the general formula (VI)) in the first two steps (1) and (2), x is the amount of thionyl chloride in step (1) and y is the amount of thionyl chloride additionally used in step (2).

In the process according to the invention, the value of z is more preferably between 2.5 and 14 and most preferably between 2.5 and 9.

If the total amount of thionyl chloride (z) is divided in steps (1) and (2) of the process according to the invention, the following specifications apply:

The value of x is between 1 and 20, preferably between 1 and 10, more preferably between 1 and 5, with the abovementioned values for z.

In the first stage, (1), the succinic monoamides of the general formula (VI)

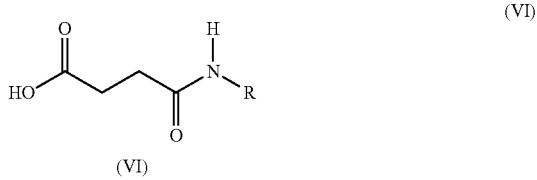

(VI)

in which R is $R^1$ or $R^2$ are reacted with thionyl chloride to give a liquid reaction mixture.

In the second stage (2), the reaction mixture formed is heated, optionally with further thionyl chloride.

Abatement of the evolution of gas is followed by the conversion of the reaction mixture to the dithiinetetracarboximides in the third step, (3), of the process. In this step, optionally after removing excess thionyl chloride, the resulting intermediate is dissolved in a diluent, admixed with water and converted to the dithiinetetracarboximides of the formula (I) by heating in this mixture.

In this way, the dithiinetetracarboximides of the formula (I) can be obtained in a technically simple and economic process, the excess of thionyl chloride being removed and the constant offgas flow allowing technically simple reprocessing of the offgases.

The succinic monoamides used as starting materials in the performance of the process according to the invention are defined in general terms by the formula (VI). R represents the definitions of $R^1$ or $R^2$.

In one embodiment (A-I) of the compound of the general formula (VI), $R^1$ and $R^2$ are the same or different and are each hydrogen, optionally mono- or poly-fluorine-, -chlorine-, -bromine-, —$OR^3$—, —$COR^4$-substituted $C_1$-$C_6$-alkyl, optionally mono- or poly-chlorine-, -methyl- or -trifluoromethyl-substituted $C_3$-$C_7$-cycloalkyl, in each case optionally mono- or poly-fluorine-, -chlorine-, -bromine-, -methyl-, -trifluoromethyl-, —$COR^4$—, -sulphonylamino-substituted phenyl or phenyl-($C_1$-$C_4$-alkyl).

In one embodiment (A-I-1) of the compound of the general formula (VI), $R^1$ and $R^2$ are the same or different and are each hydrogen, optionally mono- or poly-fluorine-, -chlorine-, -hydroxyl-, -methoxy-, -ethoxy-, -methylcarbonyloxy-, -carboxyl-substituted $C_1$-$C_4$-alkyl, optionally mono- or poly-chlorine-, -methyl- or -trifluoromethyl-substituted $C_3$-$C_7$-cycloalkyl, in each case optionally mono- to tri-fluorine-, -chlorine-, -bromine-, -methyl-, -trifluoromethyl-, —$COR^4$—, -sulphonylamino-substituted phenyl, benzyl, 1-phenethyl, 2-phenethyl or 2-methyl-2-phenethyl.

In one embodiment (A-I-2) of the compound of the general formula (VI), $R^1$ and $R^2$ are the same or different and are each hydrogen, methyl, ethyl, n-propyl, isopropyl, 2,2-difluoroethyl, 2,2,2-trifluoroethyl, in each case optionally chlorine-, methyl- or trifluoromethyl-substituted cyclopropyl or cyclohexyl.

In one embodiment (A-I-3) of the compound of the general formula (VI), $R^1$ and $R^2$ are both methyl.

Embodiment (B-I): compound of the general formula (VI) corresponding to embodiments (A-I) or (A-I-1) or (A-I-2) in which $R^3$ is hydrogen, methyl, ethyl, methylcarbonyl, ethylcarbonyl or optionally mono- or poly-fluorine-, -chlorine-, -methyl-, -ethyl-, -n-propyl-, -isopropyl- or -trifluoromethyl-substituted phenyl.

Embodiment (B-I-1): compound of the general formula (VI) corresponding to embodiments (A-I) or (A-I-1) or (A-I-2) in which $R^3$ is hydrogen, methyl, methylcarbonyl or phenyl.

Embodiment (C-I): compound of the general formula (VI) corresponding to embodiments [(A-I) or (A-I-1) or (A-I-2)] and/or [(B-I) or B(B-I-1)] in which $R^4$ is hydroxyl, methyl, ethyl, methoxy or ethoxy.

Embodiment (C-I-1): compound of the general formula (VI) corresponding to embodiments [(A-I) or (A-I-1) or (A-I-2)] and/or [(B-I) or B(B-I-1)] in which $R^4$ is hydroxyl or methoxy.

Particular preference is given to using N-methylsuccinamide as the starting material, as a result of which the compound (I-1) obtained as the end product is 2,6-dimethyl-1H,5H-[1,4]dithiino[2,3-c:5,6-c']dipyrrole-1,3,5,7(2H,6H)-tetrone.

If N-tert-butylsuccinamide is used as the starting material, the compound (I-2) obtained as the end product is 2,6-di-tert-butyl-1H,5H-[1,4]dithiino[2,3-c: 5,6-c]dipyrrole-1,3,5,7 (2H,6H)-tetrone.

If N-cyclohexylsuccinamide is used as the starting material, the compound (I-3) obtained as the end product is 2,6-dicyclohexyl-1H,5H-[1,4]dithiino dipyrrole-1,3,5,7(2H,6H)-tetrone.

If N-propylsuccinamide is used as the starting material, the compound (I-4) obtained as the end product is 2,6-dipropyl-1H,5H-[1,4]dithiino dipyrrole-1,3,5,7(2H,6H)-tetrone.

Step (1) of the process according to the invention is performed continuously or batchwise, preference being given to performing step (1) continuously.

The reaction temperature in the first step, (1), of the process according to the invention can be varied within wide limits and is between −20° C. and 50° C., preferably at temperatures of −5° C. to 30° C.; more preferably of −5° C. to 10° C.

Step (2) of the process according to the invention is performed continuously or batchwise. Preference is given to conducting step (2) of the process continuously.

Suitable apparatuses for the continuous performance of the process steps according to the invention are the various continuous apparatuses familiar to those skilled in the art. Examples of such continuous apparatuses are:
a) continuous stirred tanks, optionally connected in series to give a stirred tank cascade,
b) tubular reactor,
c) thin-film evaporator,
d) reactive rectifier,
e) microreactor,
f) crossflow reactor,
g) circulation or loop reactors,
or combinations of various continuous reactors.

Preference is given to the use of a stirred tank cascade, tubular reactor or thin-film evaporator, particular preference to the use of a stirred tank cascade.

The reaction temperature in the second step, (2), of the process according to the invention can be varied within wide limits and is between 0° C. and 150° C., preferably at temperatures of 20° C. to 120° C.; more preferably of 30° C. to 100° C.

The residence time in the second step, (2), of the process according to the invention is between 1 minute and 24 hours. The residence time is preferably between 15 minutes and 10 hours, more preferably between 30 minutes and 6 hours.

The first step, (1), and the second step, (2), of the process according to the invention can optionally be performed in the presence of a diluent which is very substantially inert under the reaction conditions. Examples of such diluents include aliphatic hydrocarbons such as pentane, hexane, heptane, cyclohexane, methylcyclohexane, chlorinated hydrocarbons such as methylene chloride, chloroform, 1,2-dichloroethane, aromatic hydrocarbons such as toluene, xylene, mesitylene, chlorinated aromatic hydrocarbons such as chlorobenzene, dichlorobenzene, ethers such as diethyl ether, methyl tert-butyl ether, tetrahydrofuran, dioxane, nitriles such as acetonitrile, propionitrile, butyronitrile, esters such as methyl acetate and ethyl acetate. Preference is given to methylene chloride, chloroform or 1,2-dichloroethane, toluene, xylene or chlorobenzene. It is preferable to perform the two process steps (1) and (2) without diluents.

Any diluent present is preferably likewise distilled off under reduced pressure in step (2) of the process according to the invention.

Step (3) of the process according to the invention is performed continuously or batchwise.

In the third step, (3), of the process according to the invention, the intermediate obtained, optionally after removal of the diluent and/or excess thionyl chloride, is dissolved in a diluent and converted by heating in this solvent, optionally with addition of water, to the dithiinetetracarboximides of the formula (I). The reaction mixture is preferably stirred during this time.

In the third step, (3), of the process according to the invention, an organic solvent or a solvent mixture is used.

These solvents are preferably at least partly miscible with water. In the case of solvents of poor or zero water miscibility, miscibility can be achieved by means of selected solubilizers (e.g. phase transfer catalyst).

Suitable diluents for the third step, (3), of the process according to the invention are specifically water, dimethyl sulphoxide, sulpholane, alcohols, for example methanol, ethanol, propanol, isopropanol, 1-butanol, 2-butanol, isobutanol, tert-butanol, 1-pentanol, cyclopentanol, cyclohexanol, ethylene glycol, ethylene glycol monomethyl ether, hydrocarbons such as hexane, heptane, cyclohexane, methylcyclohexane, toluene, xylenes, mesitylene, chlorobenzene, dichlorobenzene, nitrobenzene, esters such as methyl acetate, ethyl acetate, amides such as formamide, N,N-dimethylformamide; N,N-dimethylacetamide, N-methylpyrrolidone, ethers such as methyl tert-butyl ether, tetrahydrofuran, 1,4-dioxane, nitriles such as acetonitrile, propionitrile, butyronitrile, benzonitrile, ketones such as acetone, methyl ethyl ketone, methyl isobutyl ketone, pinacolone, carboxylic acids such as formic acid, acetic acid, propionic acid, or mixtures of these diluents.

Preference is given to water, toluene, dimethyl sulphoxide, methanol, ethanol, propanol, isopropanol, 1-butanol, 2-butanol, isobutanol, tert-butanol, 1-pentanol, cyclohexanol, ethylene glycol, methyl acetate, N,N-dimethylformamide, N,N-dimethylacetamide, tetrahydrofuran, 1,4-dioxane, acetonitrile, acetone, methyl ethyl ketone, methyl isobutyl ketone, acetic acid, or mixtures of these diluents.

Particular preference is given to mixtures of water and toluene, methanol, ethanol, propanol, isopropanol, 1-butanol, 2-butanol, isobutanol, 1-pentanol, methyl acetate, tetrahydrofuran, 1,4-dioxane, acetonitrile, acetone or acetic acid.

The mixing ratio of water to organic solvent can be varied within wide limits from, for example, 9:1 to 1:9.

The reaction temperature in the third step, (3), of the process according to the invention can be varied within wide limits and is between 0° C. and 180° C., preferably at temperatures of 40° C. to 140° C.; more preferably of 40° C. to 120° C.

The reaction time in the third step, (3), of the process according to the invention is between 1 minute and 24 hours, preferably from 15 minutes to 12 hours, more preferably from 1 to 6 hours.

The process according to the invention is illustrated by the examples which follow, without being restricted thereto.

Example 1

Use of a Thin-Film Evaporator in the Second Step (2) of the Process According to the Invention A reaction mixture of 10 g [74.5 mmol] of N-methylsuccinamide in 74.7 g [596.6 mmol] of thionyl chloride (content: 95%) is introduced within 2 hours into a thin-film evaporator heated to casing temperature 90° C. (diameter: 6 cm, length: 30 cm, wiper speed: 350 rpm). A constant offgas flow is observed. 20 g of a brown oil are obtained in the bottoms vessel, and 39.7 g of thionyl chloride in the distillate vessel (corresponding to 89.4% of the excess). The brown oil is heated at reflux together with 20 ml of toluene and 0.15 g of Aliquat 336 for 4 hours. After cooling, the solids are filtered off with suction, washed with water and ethanol, and dried. This gives 5.8 g of compound I (R=Me).

Example 2

Use of a Column with Random Packing in the Second Step (2) of the Process According to the Invention A reaction mixture of 150 g [1.14 mol] of N-methylsuccinamide in 243 g [2.02 mmol] of thionyl chloride (content: 99%) is metered into the top of a column with random packing, heated to casing temperature 77° C. (random packings=Raschig rings: length 10 mm, width 8 mm, wall thickness 1 mm; column length: approx.

110 cm, internal diameter: approx. 5 cm) with a reflux condenser connected on top within 285 min 412 g of thionyl chloride (content: 99%) are distilled in countercurrent, and this is adjusted to room temperature in a bottoms vessel at the base of the column. The top temperature is kept within the temperature range of approx. 50-60° C. A constant offgas flow is observed. The end of the metered addition is followed by cooling. A black reaction mixture which is obtained in the bottoms vessel is concentrated on a rotary evaporator at approx. 40 mbar and 60° C. The concentrated material is heated at reflux together with 190 g of toluene and 9 g of Aliquat 336 for 4 hours. After cooling, the solids are filtered off with suction, washed with water and ethanol, and dried. This gives 99 g of compound I (R=Me).

Example 3

Use of a Stirred Tank Cascade in the Second Step (2) of the Process According to the Invention Two stirred glass tanks are connected to one another via a hose, such that any volume of reaction mixture over and above 600 ml in the first tank overflows automatically into the second tank. The second tank can be emptied in a continuous and controlled manner via a base outlet into a receiver vessel.

For the continuous reaction method of stage 2, stage 1 is first produced separately, by reaction of 200 g of N-methylsuccinamide (1.52 mol) with 322 g of thionyl chloride (content: 100%, 2.71 mol) at −10° C. to −5° C. in each of 3 batches. On completion of reaction, the liquid reaction mixture is brought to room temperature.

To start up the reaction cascade, the first tank is charged with 544 g of thionyl chloride (4.57 mol) and adjusted to 70° C. One batch from stage 1 (see above) is metered into this within 5 h, until the evolution of gas has ended. The total volume in tank 1 reaches the overflow.

Subsequently, the two other batches from stage 1 are each mixed with 544 g of thionyl chloride (content: 100%, 4.57 mol) and metered into tank 1 within 7.5 h. In the course of this, the reaction mixture runs continuously into the second tank. As soon as a hold-up of 100 ml has been attained in the second tank, there is continuous discharge from this tank into a receiver. The internal temperature in reactor 1 is 65-70° C., and that in reactor 2 80-83° C. The residence time in reactor 1 averages 3 h, and that in reactor 2 0.5 h. Simultaneously, all offgases from the two reactors are conducted together through a gas flow meter. After a brief initiation period, the gas volumes which form are very homogeneous (see FIG. 1).

In FIG. 1, the total amount of the offgases in ltr (y axis) is plotted against the amount of reaction mixture metered in in ml (x axis).

The material flowing out of reactor 2 is concentrated and supplied to the third step (3) for final conversion to compound I. By way of example, the fraction of 218 to 311 g of the stage 2 product flowing out of tank 2 was initially charged in 114 g of toluene, and 13.1 g of Aliquat 336 were added. At 55-60° C., 91 g were slowly added dropwise. Subsequently, the mixture was left to stir at 80° C. for 4 h. After cooling to room temperature, the solid product was filtered off with suction on a suction filter and washed with 200 ml of water and then with several portions of ethanol, and dried. 62.4 g of dark green solids were obtained, 68% of theory. After the experiment had been completed, a total of 465.7 g of compound I (71% of theory) were obtained from all product fractions after workup.

Comparative Example 1

5.24 g [40 mmol] of N-methylsuccinamide are initially charged, and 47.6 g [400 mmol] of thionyl chloride are added dropwise at 15° C. The mixture is then heated to 80° C. and stirred at this temperature for 1 hour. Evolution of gas sets in, becoming more intense and decreasing again after a while. The reaction mixture is concentrated on a rotary evaporator. The residue (thick dark brown oil) is admixed with 100 ml of methanol/water (1:1) and heated to 60° C. for 4 hours. The mixture is then allowed to cool to room temperature, and the precipitated solids are filtered off with suction and washed with water and methanol Drying results in 4.05 g of dark green solids which, according to HPLC analysis, consist to an extent of 97.8 area % of the compound (I-1), corresponding to a yield of 70% of theory.

Comparative Example 2

243.1 g [2.02 mmol] of thionyl chloride (content: 99%) are initially charged at 10° C., and 150 g [1.14 mol] of N-methylsuccinamide are added in portions. After the reaction has ended, the cooled liquid reaction mixture is metered into a reactor which has been initially charged with 412 g of thionyl chloride (content: 99%; 3.42 mol) at 65-70° C. In the course of metered addition, the temperature is kept within the range of 65-70° C. Evolution of gas sets in, becoming more intense and decreasing again after a while. The reaction mixture is concentrated on a rotary evaporator. The residue (thick dark brown oil) is admixed with 190 ml of toluene, 161 g of water and 9.2 g of Aliquat 336, and heated to 75-80° C. for approx. 6 hours. The mixture is then allowed to cool to room temperature, and the precipitated solids are filtered off with suction and washed with water and ethanol Drying results in 118 g of dark green solids which, according to HPLC analysis, consist to an extent of 98.2 w % of the compound (I-1), corresponding to a yield of 72% of theory.

The invention claimed is:
1. A process for preparing a dithiinetetracarboximide of formula (I)

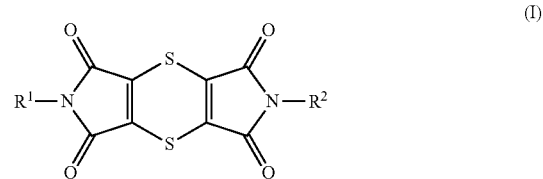

in which
$R^1$ and $R^2$ are the same or different and are each
(i) hydrogen,
(ii) optionally mono- or poly-halogen-, —$OR^3$—, —$COR^4$-substituted $C_1$-$C_8$-alkyl, (iii) optionally mono- or poly-halogen-, —$C_1$-$C_4$-alkyl- or —$C_1$-$C_4$-haloalkyl-substituted $C_3$-$C_7$-cycloalkyl,
(iv) optionally mono- or poly-halogen-, —$C_1$-$C_4$-alkyl-, —$C_1$-$C_4$-haloalkyl-, —$COR^4$—or -sulphonylamino-substituted aryl, or
(v) aryl-($C_1$-$C_4$-alkyl),
$R^3$ is hydrogen, $C_1$-$C_4$-alkyl, $C_1$-$C_4$-alkylcarbonyl, or (vi) optionally mono- or poly-halogen-, —$C_1$-$C_4$-alkyl- or —$C_1$-$C_4$-haloalkyl-substituted aryl,
$R^4$ is hydroxyl, $C_1$-$C_4$-alkyl, or $C_1$-$C_4$-alkoxy,
comprising:
(1) reacting a succinic monoamide of formula (VI)

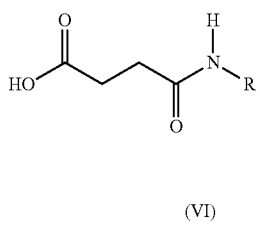

(VI)

in which R is $R^1$ or $R^2$
with thionyl chloride to give a reaction mixture,
(2) heating the reaction mixture formed in a second stage (2), and then
(3) converting the reaction mixture to one or more dithiinetetracarboximides in a third stage (3),
with continuous performance of at least one of (1), (2) and/or (3).

2. The process according to claim 1, wherein the total amount of thionyl chloride (z) is from 2.5 to 20 mol per mole of succinic monoamide of the formula (VI), where z is defined by the relationship $z=x+y$ and
z is a total amount of thionyl chloride (mol of thionyl chloride per mole of succinamide of formula (VI)) in (1) and (2),
x is the amount of thionyl chloride in (1) and
y is the amount of thionyl chloride additionally used in (2).

3. The process according to claim 2, wherein the value z is from 2.5 to 14 mol per mole of succinic monoamide of the formula (VI).

4. The process according to claim 2, wherein the value z is from 2.5 to 9 mol per mole of succinic monoamide of the formula (VI).

5. The process according to claim 2, wherein the amount of thionyl chloride x in (1) is from 1 to 20 mol per mole of succinic monoamide of the formula (VI).

6. The process according to claim 1, wherein abatement of evolution of gas in (2) is followed by conversion of the reaction mixture to one or more dithiinetetracarboximides in (3).

7. The process according to claim 6, wherein a resulting intermediate is dissolved in a diluent, admixed with water to form a mixture and converted to one or more dithiinetetracarboximides of the formula (I) by heating in said mixture.

8. The process according to claim 1, wherein (1) is performed continuously.

9. The process according to claim 1, wherein (2) is performed continuously.

10. The process according to claim 1, wherein an organic solvent at least partly miscible with water is used in (3).

11. The process according to claim 1, wherein at least one solvent used in (3) comprises water, dimethyl sulphoxide, sulpholane, alcohols optionally comprising methanol, ethanol, propanol, isopropanol, 1-butanol, 2-butanol, isobutanol, tert-butanol, 1-pentanol, cyclopentanol, cyclohexanol, ethylene glycol, ethylene glycol monomethyl ether, hydrocarbons optionally comprising hexane, heptane, cyclohexane, methylcyclohexane, toluene, xylenes, mesitylene, chlorobenzene, dichlorobenzene, nitrobenzene, esters optionally comprising methyl acetate, ethyl acetate, amides such as formamide, N,N-dimethylformamide; N,N-dimethylacetamide, N-methylpyrrolidone, ethers optionally comprising methyl tert-butyl ether, tetrahydrofuran, 1,4-dioxane, nitriles optionally comprising acetonitrile, propionitrile, butyronitrile, benzonitrile, ketones optionally comprising acetone, methyl ethyl ketone, methyl isobutyl ketone, pinacolone, carboxylic acids optionally comprising formic acid, acetic acid, propionic acid, or a mixture thereof.

12. The process according to claim 1, wherein (3) is performed at a reaction temperature from 40° C. to 120° C.

13. The process according to claim 1, wherein (3) is performed continuously.

14. The process according to claim 2, wherein additional thionyl chloride is used in (2).

* * * * *